United States Patent [19]
Churchill et al.

[11] Patent Number: 4,877,606
[45] Date of Patent: Oct. 31, 1989

[54] BIODEGRADABLE AMPHIPATHIC COPOLYMERS

[75] Inventors: Jeffrey R. Churchill, Northwich; Francis G. Hutchinson, Lymm, both of United Kingdom

[73] Assignee: Imperial Chemical Industries PLC, London, England

[21] Appl. No.: 145,116

[22] Filed: Jan. 19, 1988

Related U.S. Application Data

[62] Division of Ser. No. 747,173, Jun. 21, 1985, Pat. No. 4,745,160.

[30] Foreign Application Priority Data

Jun. 26, 1984 [GB] United Kingdom ................. 8416234

[51] Int. Cl.$^4$ .............................................. A61K 47/00
[52] U.S. Cl. ........................................ 424/78; 424/81; 424/486; 523/309
[58] Field of Search .................... 523/309; 424/78, 81, 424/486

[56] References Cited

U.S. PATENT DOCUMENTS

| | | | |
|---|---|---|---|
| 3,651,008 | 3/1972 | Moser et al. | 523/309 |
| 3,773,919 | 11/1973 | Boswell | 424/19 |
| 3,887,699 | 6/1975 | Yolles | 424/19 |
| 4,018,736 | 4/1977 | Fabian et al. | 523/309 |
| 4,526,938 | 7/1986 | Chruchill | 525/415 |

FOREIGN PATENT DOCUMENTS 58481 8/1982 European Pat. Off. .

OTHER PUBLICATIONS

"Dictionary of Science and Technology": Editor T. C. Collocott M. A. W. & R. Chambers (1971).
"Concise Chemical and Technical Dictionary" Edited by H. Bennett, F.A.I.C., Director, B. R. Laboratories (1986).

Primary Examiner—Allan M. Lieberman
Attorney, Agent, or Firm—Cushman, Darby & Cushman

[57] ABSTRACT

A pharmaceutically or veterinarily acceptable amphipathic, non-cross linked linear, branched or graft block copolymer, which has a minimum weight average molecular-weight of 1000, in which the hydrophobic component is biodegradable or hydrolytically unstable under normal physiological conditions, and the hydrophilic component may or may not be biodegradable or hydrolytically unstable under such conditions, and which copolymer is self-dispersible in water; together with mixtures of such a copolymer and a drug, which may be water-soluble or water-insoluble, which mixtures are self-dispersible in waterf; and processes for the manufacture of such copolymers and such mixtures.

1 Claim, No Drawings

BIODEGRADABLE AMPHIPATHIC COPOLYMERS

This is a division of application Ser. No. 747,173, filed June 21, 1985, now U.S. Pat. No. 4,745,160.

This invention relates to biodegradable amphipathic copolymers, and in particular it relates to such copolymers which are rapidly self-dispersible in water to form stable dispersions.

Such copolymers are useful in the manufacture of continuous release formulations of drugs, and are particularly useful for the manufacture of such formulations in which the drug is sensitive to denaturation or degradation by exposure to organic solvents, non-neutral pH or elevated temperature, for example many polypeptide drugs. The copolymers of the present invention permit the manufacture of continuous release formulations of these drugs under conditions which avoid non-neutral pH and elevated temperature, and under conditions such that exposure to organic solvents is avoided, or reduced to minimal levels in solvent mixtures containing only a small proportion of organic solvent.

It is to be understood that in this specification the term "self-dispersible" as applied to a copolymer means a copolymer which, when added to water disperses to form a stable dispersion, without the addition of any surfactant or other additive. In this context, a "stable" dispersion is one which does not significantly agglomerate or precipitate within the time normally required to process the copolymer into a continuous release drug formulation, say 24 hours.

Boswell and Scribner, in U.S. Pat. No. 3,773,919, and Yolles, in U.S. Pat. No. 3,887,699, have described the use of biodegradable polymers, in particular polylactide and poly(lactide co-glycolide), in the manufacture of sustained release pharmaceutical formulations, and although their disclosures include some polypeptide drugs, we have found that the conditions of manufacture, involving a temperature of at least 130° C., are sufficient to almost completely decompose many polypeptide drugs, so that satisfactory continuous release formulations are not obtainable using the technology of these United States patents.

Furthermore, Hutchinson in European Patent Specification No. 58481 disclosed that, even if processed differently, so as to avoid decomposition of the polypeptide drug, the copolymers described by Boswell and Scribner, and by Yolles, could not be used to obtain satisfactory continuous release formulations of polypeptides. Rather, the release profile was biphasic and discontinuous, an initial release period resulting from surface leaching of the polypeptide being followed by a prolonged "dead phase", in which none or very little, was released, followed in turn by the major release of the polypeptide consequent upon the copolymer matrix absorbing water and being biodegraded.

Hutchinson did, however, disclose that satisfactory continuous release formulations of some polypeptides could be made by using polylactide or poly (lactide co-glycolide) of generally lower molecular weights than those disclosed by Boswell and Scribner, and Yolles, and at lower temperature, but the processing still required the use of organic solvents, to which many polypeptides are labile.

Churchill and Hutchinson in European Patent Specification No. 92918 U.S. Pat. No. 4,526,938 have disclosed the use of biodegradable amphipathic copolymers, of the general types used in the present invention, in the manufacture of continuous release formulations. However, the copolymers there described are not self-dispersible in water to form stable dispersions, but require the use of organic solvents, which, as indicated above, can be denaturing to polypeptides, in the subsequent processing into a continuous release formulations.

It is an object of the present invention to provide a biodegradable amphipathic copolymer which is self-dispersible in water, and which can therefore be used to manufacture continuous release formulations of drugs without recourse to the use of high temperatures or non-neutral pH, and, for water-soluble drugs such as polypeptides, without exposure of the drug to the use of organic solvents during manufacture. Such copolymers may be self-dispersible as initially synthesised, or copolymers which are not inherently self-dispersible may be rendered so by the processes described herein.

The biodegradable amphipathic copolymers of this invention are also useful for the manufacture of sustained continuous release injectable formulations of drugs which, in contrast with polypeptides, are of low molecular weight and low water solubility. For such drugs, the copolymers of this invention act as very efficient dispersing agents, and can give colloidal suspensions which can be administered by injection to give sustained continuous delivery of lipophilic drugs.

In addition, the biodegradable amphipathic copolymers of this invention can be used to manufacture drug formulations which are targetable to particular organs in the human or animal body. It is known that particles or microspheres of different sizes accumulate in different organs of the body after intravenous injection, depending upon the size of the particles injected. (For a review, see Tomlinson, "Microsphere Delivery Systems For Drug Targeting And Controlled Release" in Int. J. Pharm. Tech. and Prod. Mfr., 4,(3), p49–57, 1983). For example, particles of less than 50 nm can pass through the fenestrations of the liver endothelium and become localised, perhaps after lymphatic transport, in the spleen, bone marrow and possibly tumour tissue. Intravenous, intra-arterial or intraperitoneal injection of particles of approximately 0.1 to 2.0 $\mu$m. leads to a rapid clearance of particles from the blood stream by macrophages of the reticuloendothelial system, with eventual localisation of these in the lyosomes of the Kuppfer cells of the liver. Intravenous delivery of particles above 7–12 $\mu$m. leads to mechanical filtration by the lungs, while particles between 2 and 12 $\mu$m. will become entrapped within the capillary networks of not only the lung but also the liver and spleen. Intra-arterial delivery of particles greater than 12 $\mu$m. leads to their blockage of the first capillary bed encountered. The copolymers of this invention can be used to manufacture dispersions of controlled particle size, which can be organ-targeted in the manner described above.

Scheme 1 illustrates diagrammatically the processes involved in this invention.

SCHEME I

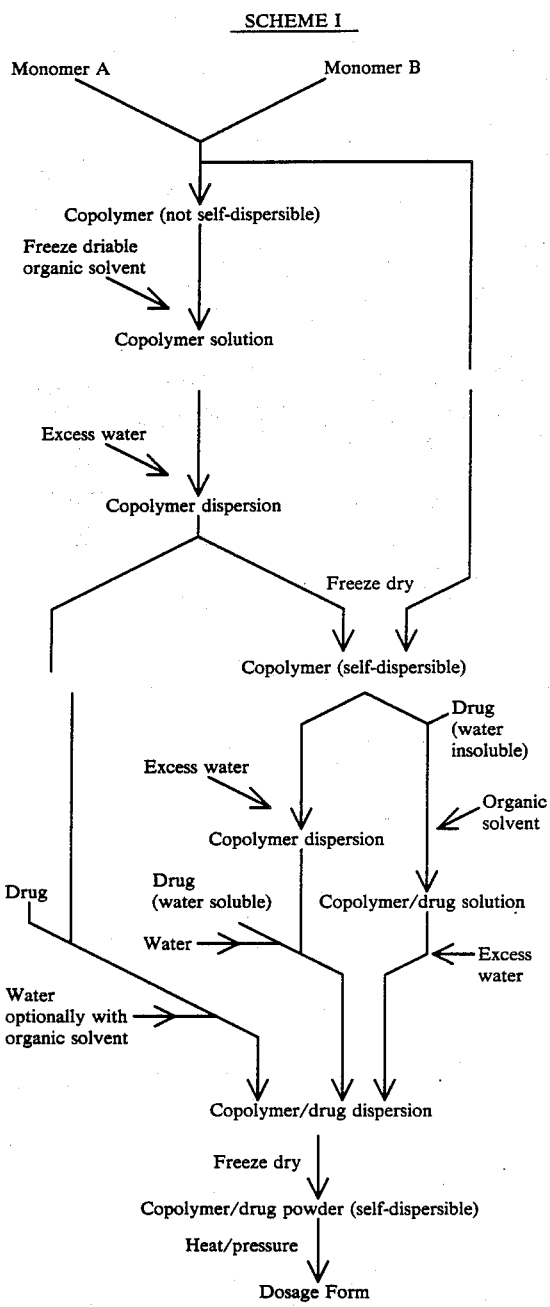

Thus, according to the invention, there is provided a pharmaceutically or veterinarily acceptable amphipathic, non-cross-linked linear, branched or graft block copolymer, which has a minimum weight average molecular weight of 1000, in which the hydrophobic component is biodegradable or hydrolytically unstable under normal physiological conditions, and the hydrophilic component may or may not be biodegradable or hydrolytically unstable under such conditions, characterised in that it is self-dispersible in water to form a stable dispersion.

According to a further feature of the invention, there is provided a process for the manufacture of a self-dispersible copolymer as defined above, which comprises freeze-drying a frozen stable aqueous dispersion of a pharmaceutically or veterinarily acceptable amphipathic, non-cross-linked linear, branched or graft block copolymer, which has a minimum weight average molecular weight of 1000, in which the hydrophobic component is biodegradable or hydrolytically unstable under such conditions, and the hydrophilic component may or may not be biodegradable or hydrolytically unstable under such conditions.

When an "aqueous dispersion" is referred to herein, it is to be understood as comprising a dispersion in water alone, or in water containing a small proportion, for example up to 10%, of a water-miscible organic solvent.

The copolymers which may be used as the starting materials in the above process are those described in European Patent Specification No. 92918, referred to above.

The frozen, stable aqueous dispersion used as the starting material for the above process may be obtained by dissolving the copolymer described immediately above, in its non-self-dispersible form, as initially synthesised, in a minimum amount of a water-miscible solvent, which either has a low boiling point, say below 100° C., for example methanol or ethanol, or is freeze-driable, for example dioxan or acetic acid, vigorously agitating said solution while an excess of water is added slowly, to form an extremely fine, stable aqueous dispersion, and then freezing said dispersion.

According to a further feature of the invention, there is provided a solid, copolymer/drug powder material comprising up to 99% by weight of a drug, the remainder being a pharmaceutically or veterinarily acceptable amphipathic, non-cross-linked linear, branched or graft block copolymer as defined above, characterised in that said solid, powder material is self-dispersible in water to form a stable dispersion.

According to a further feature of the invention, there is provided a process for the manufacture of a solid, copolymer/drug powder material, as defined immediately above, which comprises freeze-drying a frozen, stable aqueous dispersion of the copolymer and the drug.

The frozen, stable aqueous dispersion used as the starting material for the above process may be obtained, when the drug is water-soluble, for example a polypeptide, by dispersing a self-dispersible copolymer, as defined above, in water, buffering the dispersion to physiological or neutral pH, mixing the buffered dispersion with an aqueous solution of the water-soluble drug, and freezing the resulting copolymer/drug dispersion.

Particular water-soluble polypeptides which may be used in this invention are, for example, oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

When the drug is water-insoluble, the frozen, stable aqueous dispersion used in the above process may be obtained by dissolving the drug and the self-dispersible copolymer in a minimum amount of a water-miscible organic solvent, for example dioxan, acetic acid, acetonitrile, methanol or ethanol, slowly adding an excess of water to the vigorously agitated solution to produce a fine, stable dispersion, and then freezing the dispersion.

Any drug of low water-solubility is appropriate for use in this aspect of the invention.

Alternatively, one of the freeze-drying processes may be avoided by taking the copolymer in its non-self-dispersible form, dissolving it in a watermiscible organic solvent, precipitating it as a fine dispersion by slow addition of an excess of water with vigorous agitation, adding a solution of a drug, either in water, if the drug is water-soluble, or in a water miscible organic solvent or in a mixture thereof with water if the drug is water-insoluble, to the copolymer dispersion, and then freezing and freeze-drying the total mixture.

Certain pharmaceutically or veterinarily acceptable amphipathic, non-cross-linked linear, branched or graft block copolymers, which have a minimum weight average molecular weight of 1000, in which the hydrophobic component is biodegradable or hydrolytically unstable under normal physiological conditions, and in which the hydrophilic component may or may not be biodegradable or hydrolytically unstable under such conditions, are self-dispersible in water as synthesised. These are copolymers which contain a large proportion, that is, more than 50%, of hydrophile relative to hydrophobe, or copolymers in which the hydrophobe is of low molecular weight, for example $M_w$ of less than 5000.

Additionally, the structure of the copolymer, and the nature of the individual hydrophilic and hydrophobic polymers therein, control the degree of self-dispersibility in water of the copolymer obtained therefrom. Thus, for example, polylactide-graft-polyvinylpyrrolidone (PVP) is self-dispersing when it contains 50% or more of PVP, even though the polylactide may be of relatively high molecular weight, for example $M_w$ of greater than 30,000; and polylactide/polyethylene glycol 1900 (equal weights) is self-dispersible. However, polylactide/polyethylene glycol 5000 (equal weights) is self-dispersible with difficulty, and above this molecular weight the copolymers are not immediately self-dispersible in water, but require initially the addition of a small proportion of an organic solvent, which can subsequently be removed by evaporation or freeze-drying.

As indicated above, the materials of this invention are useful in the manufacture of sustained continuous release formulations of drugs. As has been described above, a mixture of a copolymer of the invention with a drug can be manufactured under such conditions that the drug is not exposed to high temperature, to non-neutral pH, to high concentrations of organic solvent, or to organic solvent at elevated temperature, and such copolymer-drug mixtures can be processed into suitable pharmaceutical or veterinary formulations by conventional procedures, for example by compression moulding at low temperatures (many can be conveniently compression moulded at about 60° C., well below the decomposition temperature of most drugs, including polypeptide drugs which are among those which are most susceptible to decomposition at elevated temperatures), to form implantable depot formulations as described, for example, by Hutchinson (European Patent Specification No. 58481) and by Churchill and Hutchinson (European Patent Specification No. 92918), which give a sustained continuous release of the drug. Alternatively, for water-insoluble drugs, the copolymer-drug mixture can be simply dispersed into sterile water to give a fine aqueous dispersion which can be used as an injectable, sustained continuous release formulation, or, if the particle size is suitably controlled, a formulation which is targeted to a particular organ, as described above.

The particle size of such an aqueous dispersion can be controlled within fairly close limits by controlling the particle size of the copolymer used. This is achieved during the manufacture of the self-dispersible form of the copolymer used, and is achieved by suitable adjustment of the rate of addition of water to the solution of copolymer in the freeze-driable, water-miscible solvent, and control of the rate of agitation during this process. The particle size of the dispersion so obtained may be measured in conventional manner, for example by optical microscopy, Coulter counter or nanosizer.

Useful co-excipients in the manufacture of sustained, continuous release formulations of polypeptides using the above-described copolymer/drug mixtures, are low or high molecular weight, water soluble polymers which are compatible, or partially compatible therewith, such as gelatin, polyvinylpyrrolidone, dextran, polyethylene glycols, sodium alginate and water soluble, synthetic, non-therapeutic polypeptides. Such co-excipients provide additional hydrophilic regions, or pores, in the polymer matrix, and also stabilise the tertiary structure of the polypeptide by chain entanglement, which is achievable by virtue of their being compatible or partially compatible with the polypeptide.

EXAMPLE 1

Two grammes of an AB type biodegradable copolymer comprising 25% by weight of a methoxypolyethylene glycol of molecular weight 5900 (component A) and 75% by weight of poly(D,L-lactide) (component B) were dissolved in glacial acetic acid (2 ml.), and the solution was stirred vigorously while distilled water (21 ml.) was added slowly, to produce an extremely fine dispersion. The dispersion was frozen, and freeze dried at 0.01 mm. of mercury (13.3 Pa) for 24 hours, to give a dry powder copolymer.

On addition of the dry powder to water, with stirring, it redispersed to form a very fine dispersion.

EXAMPLE 2

The dry powder copolymer of Example 1 (0.5 g.) was dispersed with vigorous stirring into distilled water (5 ml.) containing sodium azide (0.01%), and the dispersion was buffered to pH8 with 0.1N sodium hydroxide. Bovine serum albumin (BSA) (0.125 g.) was dissolved in distilled water (1.0 ml.) and $^{14}$C-methylated BSA (10 ul. of a 5 uCi per ml. solution. in 0.01M sodium phosphate buffer) was added, the BSA solution was added to the copolymer dispersion, and the mixture was frozen, then freeze dried at 0.01 mm. of mercury (13.3 Pa) for 24 hours.

The freeze dried product was moulded at 60°–70° to give slabs 1 cm. square and of thickness 0.2 cm., 0.09 cm. and 0.04 cm. The different slabs were each separately immersed in 2 ml. of phosphate buffered saline (pH 7.4) containing 0.02% sodium azide, at 37° C. At intervals, the medium was removed and replaced with fresh buffer, and the radioactivity released into the removed medium was assayed.

| Time | Cumulative % BSA released | | |
|---|---|---|---|
| | 0.2 cm. slab | 0.09 cm. slab | 0.04 cm. slab |
| 1 hour | 10.8 | 23.8 | 46.6 |
| 4 hours | 23.4 | 48.5 | 77.3 |
| 24 hours | 64.4 | 86.5 | 86.7 |
| 3 days | 86.4 | 92.2 | 88.8 |
| 12 days | 90.1 | 92.3 | 90.9 |

EXAMPLE 3

2.5 Grammes of a poly (D,L-lactide-coglycolide)-graft(polyvinylpyrrolidone) copolymer, containing 50% by weight of poly (D,L-lactide-coglycolide) comprising equimolar proportions of lactide and glycolide, and 50% by weight of polyvinyl-pyrrolidone, were dissolved in glacial acetic acid (5 ml.) and stirred vigorously while distilled water (20 ml.) was added slowly, to produce a very fine dispersion, which was then frozen and freeze dried at 0.1 mm. of mercury (13.3 Pa) for 24 hours, to give a dry powder copolymer.

On addition of the dry powder copolymer to water, with stirring, it redispersed almost immediately to form a very fine dispersion.

EXAMPLE 4

2.0 Grammes of an ABA type biodegradable block copolymer comprising 80% by weight of poly(D,L-lactide) (component A) and 20% by weight of polyethylene gylcol of molecular weight 2000 (component B) was added to absolute ethanol (3 ml.) and stirred vigorously while water (1.5 ml.) was added slowly to produce an extremely fine dispersion. A further 15 ml. of water was added, with vigorous agitation, to give a dilute dispersion of the copolymer, which was then buffered to pH8 by addition of 0.1N sodium hydroxide.

Bovine serum albumin (BSA) (0.5 g.) was dissolved in water (5 ml.) and $^{14}$C-methylated BSA (70 ul. of a 5 uCi/ml. solution in 0.01M sodium phosphate) was added. The BSA solution was then mixed with the copolymer dispersion, frozen, and freeze dried at 0.01 mm. of mercury (13.3 Pa) for 30 hours.

The freeze-dried powder was moulded at 60° C. to give slabs 1 cm. square and of thickness 0.36 cm., 0.16 cm. and 0.06 cm. The different slabs were each separately immersed in 2 ml. of phosphate buffered saline, pH 7.4, at 37° C. At intervals, the medium was removed and replaced with fresh buffer, and the radioactivity released into the removed medium was assayed.

| Time | Cumulative % BSA released | | |
|---|---|---|---|
| | 0.36 cm. slab | 0.16 cm. slab | 0.06 cm. slab |
| 1 hour | 8.5 | 12.8 | 23.8 |
| 4 hours | 17.0 | 28.0 | 58.4 |
| 24 hours | 40.3 | 58.2 | 87.2 |
| 4 days | 65.8 | 82.0 | 96.0 |
| 11 days | 82.1 | 96.0 | 100 |

EXAMPLE 5

Purified methoxypolyethylene glycol of molecular weight 1900, rigorously dried at 160° C. for 1 hour at 0.1 mm. of mercury (13.3 Pa) (10 g.) and freshly prepared, rigorously dried D,L-lactide (10 g.) were stirred under nitrogen at 160° C., stannous octoate (stannous 2-ethylhexanoate) (50 ul.) was added, and the mixture was kept at 160° C. for 3 hours, to give a straw-coloured, slightly viscous liquid which solidified on cooling. The solid product (0.5 g.) was added to distilled water (5 ml.) and stirred at 37° C. for 18 hours, after which time it has formed an extremely fine dispersion or colloidal suspension, which appeared entirely clear, except for a very faint blue haze when held to the light. In contrast, a simple mixture of the same methoxypolyethyleneglycol (0.25 g.) and poly(D,L-lactic acid) (0.25 g.) in distilled water (5 ml.) did not give a dispersion after stirring at 37° C. for a similar period, but the polyester remained as a semi-solid, non-dispersed phase.

EXAMPLE 6

An AB block copolymer of poly(d,l-lactide) and methoxy-polyethylene glycol containing 50% (wt) polyester and 50% (wt) of polyether was prepared by the ring opening polymerisation of d,l-lactide in the presence of methoxypolyethylene glycol 5000 at 160° C. using an organotin catalyst.

100 mg. of the block copolymer and 10 mg. of an antioestrogen, ICI 189150, which has very low aqueous solubility, were dissolved in 0.4 ml. of glacial acetic acid, and 2 ml. of water were added slowly with vigorous agitation to give a colloidal suspension of drug/polymer in the acetic acid/water mixture. The mixture was frozen and freeze dried at 0.01 mm.Hg. (13.3 Pa) for 24 hr., to give a solid freeze dried product.

On addition of 0.9% sodium chloride solution in water the freeze dried product redispersed to give a stable dispersion suitable for injection.

What we claim is:

1. A process for the manufacture of a frozen, stable aqueous dispersion of a copolymer and a drug, the drug comprising up to 99% by weight of the copolymer plus drug content, and the copolymer comprising a pharmaceutically or veterinarily acceptable amphipathic, non-crosslinked linear, branched or graft block copolymer, which has a minimum weight average molecular weight of 1000, in which the hydrophobic component is biodegradable or hydrolytically unstable under normal physiological conditions, and the hydrophilic component may or may not be biodegradable or hydrolytically unstable under such conditions, characterized by freeze-drying a frozen, stable aqueous dispersion of the copolymer and the drug.

* * * * *